(12) United States Patent
Shelley et al.

(10) Patent No.: US 8,894,849 B1
(45) Date of Patent: Nov. 25, 2014

(54) UPWARD FLOW CONSTRUCTED WETLAND FOR TREATMENT OF WATER CONTAMINATED WITH CHLORINATED ALIPHATICS

(75) Inventors: Michael Shelley, Dayton, OH (US);
Abinash Agrawal, Fairborn, OH (US);
Ke Qin, Fairborn, OH (US); Garrett Struckhoff, Fairborn, OH (US); Carl Enfield, Crozet, VA (US); James Waldron, Colorado Springs, CO (US);
Christina Powell, Springfield, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 416 days.

(21) Appl. No.: 13/412,606

(22) Filed: Mar. 5, 2012

Related U.S. Application Data

(60) Provisional application No. 61/448,696, filed on Mar. 3, 2011.

(51) Int. Cl.
*C02F 3/30* (2006.01)
*C02F 3/32* (2006.01)
*E21B 49/10* (2006.01)
*G01N 1/16* (2006.01)
*E21B 49/08* (2006.01)
*G01N 1/12* (2006.01)
*C02F 103/06* (2006.01)
*C02F 101/36* (2006.01)

(52) U.S. Cl.
CPC ............... *C02F 3/301* (2013.01); *C02F 3/327* (2013.01); *E21B 49/10* (2013.01); *E21B 49/083* (2013.01); *C02F 2103/06* (2013.01); *G01N 1/16* (2013.01); *G01N 1/12* (2013.01); *C02F 2101/36* (2013.01); *C02F 3/303* (2013.01); *Y10S 210/903* (2013.01)
USPC ................ 210/150; 210/170.07; 210/170.08; 210/602; 210/605; 210/903; 73/864.33; 73/864.64; 166/169; 422/513; 422/534

(58) Field of Classification Search
CPC ............ C02F 3/30; C02F 3/301; C02F 3/303; C02F 3/306; C02F 3/32; C02F 3/327; C02F 2101/36; C02F 2103/06; E21B 49/081; E21B 49/083; E21B 49/10; G01N 1/12; G01N 1/16
USPC .......... 210/150, 151, 170.01, 170.07, 170.08, 210/602, 605, 617, 630, 747.1, 747.7, 903; 73/864, 864.33, 864.51, 861.64; 166/162, 169; 422/513, 534
See application file for complete search history.

(56) References Cited

U.S. PATENT DOCUMENTS

| | | | | |
|---|---|---|---|---|
| 2,852,081 | A * | 9/1958 | Lebourg ..................... | 166/169 |
| 4,415,450 | A * | 11/1983 | Wolverton ................... | 210/602 |
| 4,417,622 | A * | 11/1983 | Hyde .......................... | 166/169 |
| 5,281,332 | A * | 1/1994 | Vandervelde et al. ........ | 210/151 |
| 6,165,356 | A * | 12/2000 | Carman et al. ............... | 210/150 |
| 7,081,203 | B2 * | 7/2006 | Helm ......................... | 210/170.08 |
| 7,510,649 | B1 * | 3/2009 | Lavigne ...................... | 210/151 |

(Continued)

*Primary Examiner* — Christopher Upton
(74) *Attorney, Agent, or Firm* — AFMCLO/JAZ; Fredric Sinder

(57) ABSTRACT

An improved upward flow constructed wetland cell for treatment of water contaminated with chlorinated aliphatics is disclosed. The improvements include adding ammonia-oxidizing microorganisms to the methane-oxidizing microorganisms already present in an oxygenated root zone and adding improved pore-water sample chambers for measuring the performance of the constructed wetland cell.

1 Claim, 5 Drawing Sheets

(56) References Cited

U.S. PATENT DOCUMENTS 8,029,673 B2 * 10/2011 Bottcher .................. 210/170.08
2005/0242026 A1 * 11/2005 Morris et al. .................. 210/903
2008/0210629 A1 * 9/2008 Mankiewicz ............ 210/170.07
2012/0031205 A1 * 2/2012 Lee et al. ........................ 73/864

* cited by examiner

UPWARD FLOW CONSTRUCTED WETLAND FOR TREATMENT OF WATER CONTAMINATED WITH CHLORINATED ALIPHATICS

CROSS REFERENCE TO RELATED PATENT APPLICATIONS

This application claims priority under 35 U.S.C. §119(e) from U.S. provisional application 61/448,696, filed Mar. 3, 2011 and titled "Upward Flow Constructed Wetland for Treatment of Water Contaminated with Chlorinated Aliphatics." The invention description contained in that provisional application is incorporated by reference into this description.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to constructed wetlands for remediation of groundwater contamination, primarily chlorinated ethane solvents, and particularly to improvements for a upward flow constructed wetland cell.

In a 2007 journal article titled "Development of a Wetland Constructed for the Treatment of Groundwater Contaminated by Chlorinated Ethenes," James P. Amon, Abinash Agrawal, Michael L. Shelley, Bryan C. Opperman, Michael P. Enright, Nathan D. Clemmer, Thomas Slusser, Jason Lach, Teresa Sobolewski, William Gruner and Andrew C. Entingh, *Ecological Engineering*, Vol. 30, pp. 1-6, 2007, some of the co-inventors of the present invention, and others, described a novel upward flowing constructed wetland for removing containments from groundwater. That journal article, and all journal articles and other papers referenced in this description, are fully incorporated by reference into this description. Parts of this description may include passages from those papers, with grateful thanks to those authors, but often without specific attribution.

Chlorinated solvents are a major source of groundwater pollution in the United States and pose significant health risks where groundwater is the source of drinking water. Compounds such as perchloroethylene (PCE) and trichloroethylene (TCE) were produced in large quantities after World War II and often leaked from underground storage tanks or were disposed of improperly. Where PCE is present, TCE, isomers of dichloroethylene (DCE), and vinyl chloride (VC) are often present as daughter products of its in situ degradation. These low molecular weight chlorinated hydrocarbons are relatively insoluble and much denser than water and, as such, they readily penetrate water-saturated soils and form a pool at the bottom of an aquifer. This pool and the soil zone above it become a constant source of contaminant when groundwater moves through it and creates a plume of contamination. TCE is the most common groundwater contaminant and a major contaminant at many military bases around the country.

It had been earlier discovered that contaminants such as TCE could be broken down by naturally occurring microorganisms, triggering research on ways to utilize these organisms in bioremediation treatment systems.

A key to successful adaptation of those natural bioremediation treatment systems was that degradation of chlorinated ethenes may occur in both anaerobic and aerobic environments, but PCE can be converted to TCE only under anaerobic conditions, while chlorinated ethenes can be chemically and microbially converted to progressively less chlorinated ethenes anaerobically by reductive dechlorination.

Methane as a growth substrate has been successfully studied in a number of systems. During co-metabolic degradation of TCE with methane, the methane-oxidizing bacteria (methanotrophs) produce a non-specific enzyme, methane monooxygenase (MMO), which oxidizes methane as its substrate and can also fortuitously degrade TCE.

The 2007 journal article generally described a new upward flow constructed wetland cell for treating groundwater contaminated with chlorinated aliphatics. Although wetlands have been used for water treatment for many years, the unique concept of the new constructed wetland was upward vertical water flow through individually designed soil layers, or zones, within the constructed wetland cell to provide the required sequential conditions to sequentially alter the contaminants to produce non-hazardous by-products.

Briefly, the new upward flow constructed wetland fed contaminated ground water sequentially through, from bottom to top:

(1) a first layer of organic soil where PCE would undergo anaerobic dechlorination to TCE, DCE and VC, with methane formation.

(2) a second layer of iron rich soil where TCE, DCE and VC would undergo iron reduction degradation producing TCE+, DCE+ and VC with $CO_2$ formation.

(3) a third layer where wetland plant root zones create an oxygenated zone where methane-oxidizing microorganisms oxidize the methane and, thanks to the threshold presence of the methane, also advantageously co-metabolize and degrade the TEC, DEC and VC.

Despite the success of the upward flow constructed wetland cell, its performance can still be improved.

SUMMARY OF THE INVENTION

The present invention improves upward flow constructed wetlands by the addition of ammonia-oxidizing microorganisms and improved pore-water sample chambers.

BRIEF DESCRIPTION OF THE DRAWINGS

The teachings of the present invention will be better understood from the following drawings illustrating various aspects and example embodiments of the invention and its teachings.

DETAILED DESCRIPTION

More complete details of the present invention may be found in the following papers, collectively authored by different combinations of the inventors, and all of which are fully incorporated by reference into this description.

Christina L. Powell, *Biodegradation of Groundwater Pollutants (Chlorinated Hydrocarbons) in Vegetated Wetlands: Role of Aerobic Microbes Naturally Associated with Roots of Common Plants*, PhD Dissertation, Wright State University, 2010.

Christina L. Powell and Abinash Agrawal, "Biodegradation of Trichloroethene by Methane Oxidizers Naturally Associated with Wetland Plant Roots," *Wetlands, Vol.* 31, No. 1, pp. 45-52, 2011.

C. L. Powell, G. Nagaro, A. Agrawal, "Aerobic Cometabolic Degradation of Trichloroethene by Methane and Ammonia Oxidizing Microorganisms Naturally Associated with *Carex Comsa* Roots," *Biodegradation, Vol.* 22, No. 43, pp. 527-538, 2010.

James M. Waldron, *Characterization of Chlorinated Ethene Degradation in a Vertical Flow Constructed Wetland*, Thesis, Air Force Institute of Technology, 2007.

Figure 1:
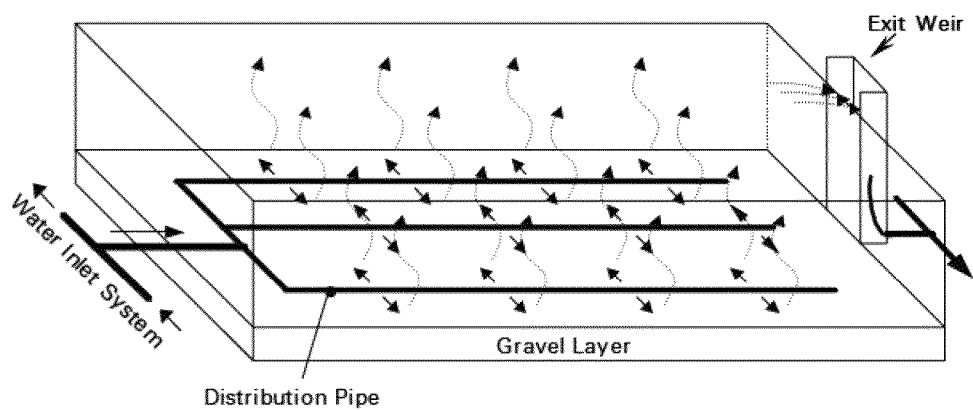
FIG. 1 shows a conceptual view of water flow through an example embodiment of a vertical constructed wet land cell according to the teachings of the present invention.

FIG. 1 is a conceptual view of water flow through an example embodiment of a vertical constructed wetland cell according to the teachings of the present invention.

Three 3" parallel, perforated PVC supply lines run along the bottom of the cell encased in a 9" thick bed of gravel consisting of crushed limestone. These lines provide a continuous supply of CE-contaminated groundwater into the treatment wetland at a rate of approximately 4.2 gallons per minute. The gravel layer was placed to allow the water entering the wetland cell to get evenly distributed across the bottom layer. A 54" thick fill, consisting mainly of soil obtained from a drained wetland nearby, was then placed on top of the gravel layer. The treatment wetland design and imposed hydraulics allows the contaminated groundwater to move upward through the soil layer to the surface, and then flow through an exit weir.

The weir is located at the opposite end of the wetland cell from the water inlet pipe and can be adjusted to control the depth of standing water on the wetland surface. The water exiting the wetland through the weir is discharged to a local sanitary sewer.

Figure 2:
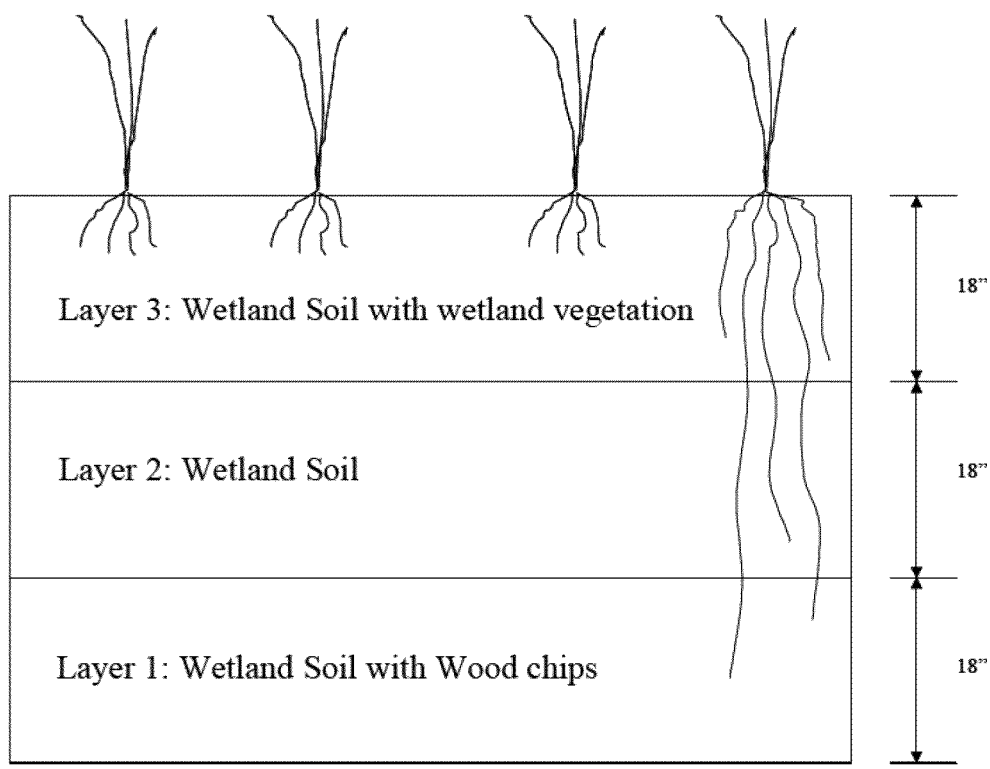
FIG. 2 shows an example soil fill within a constructed wetland overlaying a bottom gravel layer divided into three layers.

The soil fill within the constructed wetland overlies the bottom gravel layer, and it is divided into three layers, or zones, as shown in FIG. 2. The three layers are:

(a) Lower Layer—18 inches of wetland soil fill was amended with 10% wood chips (v/v) at the time of construction, to provide a source of organic carbon for inducing anaerobic (reducing) conditions quickly;

(b) Middle Layer—18 inches of un-amended wetland soil fill;

(c) Upper Layer—18 inches of un-amended wetland soil fill in which wetland vegetation was planted.

Typical wetland vegetation, such as *Carex hystercina*, *Acorus calamus*, and *Juncus effusus*, was planted on the ground surface within the cell. The original assumption was that the thickest part of the plant roots would only penetrate through the top 18 inches. However, soil cores from the field site and greenhouse experiments have shown that the roots have penetrated to a depth greater than 5 feet. Although oxygen is likely to be transported to the deeper interval of the soil layer by the root system, it is not known how much oxygen may be transported, and how the oxygen may affect microbial processes occurring in the generally anaerobic environment.

Figure 3:
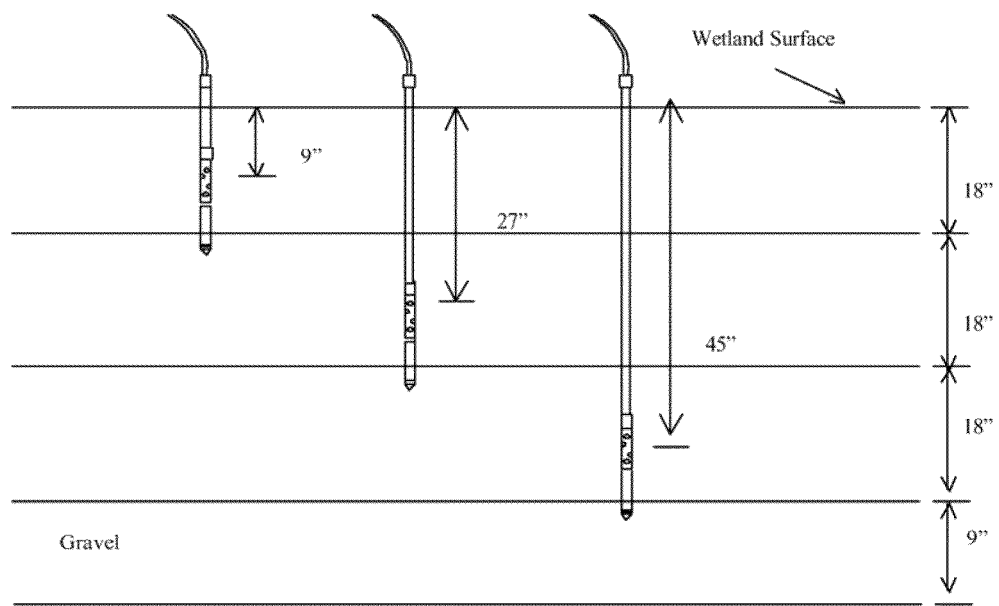
FIG. 3 shows the placement of piezometer nests in each of the lower, middle, and upper layer of a constructed wetland cell.

FIG. 3 shows the placement of piezometer nests comprising three piezometers, one screened in each of the lower, middle, and upper layer of the constructed wetland cell. The piezometers were installed so that their 6-inch screen depths were positioned in the middle of the target layer. Therefore, the average depths of the piezometers in the lower, middle, and upper layers are 45, 27, and 9 inches, respectively.

Figure 4:
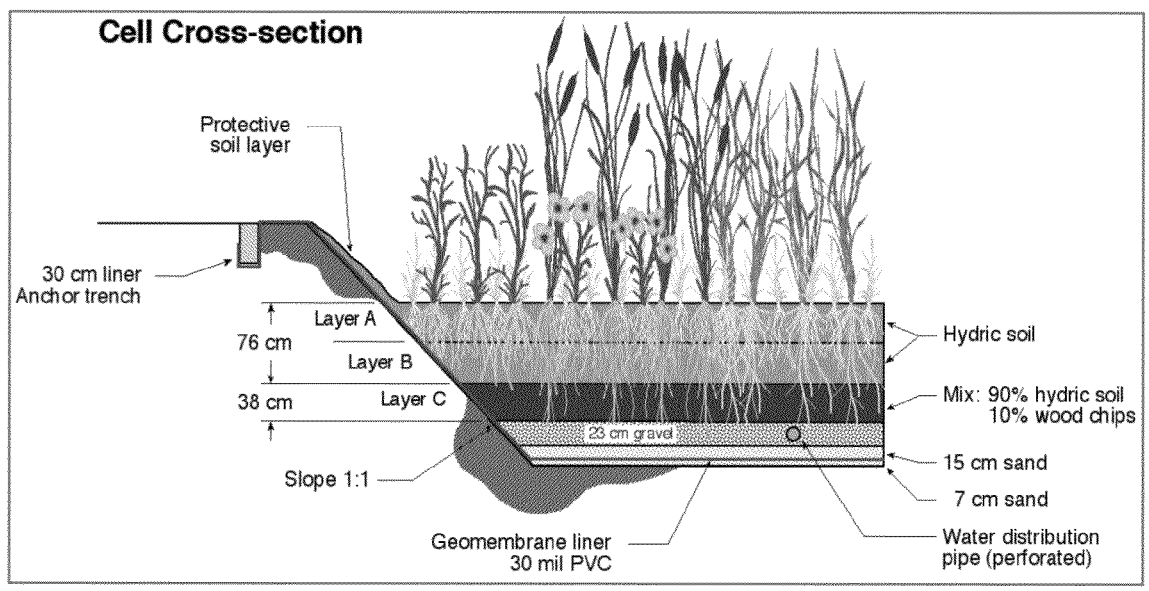
FIG. 4 is a more detailed view of an example embodiment of a upward flow constructed wetland according to the teachings of the present invention.
Figure 5:
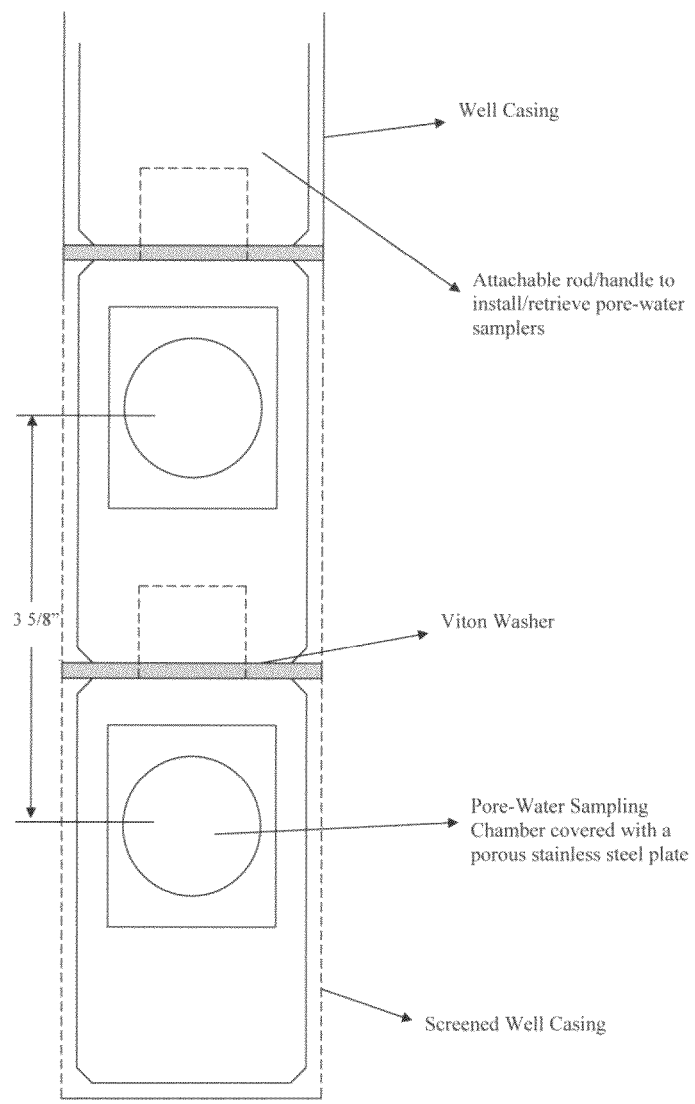
FIG. 5 is a representative view of an example embodiment of a pore-water sample cell according to the teachings of the present invention.

FIG. 4 is a more detailed view of an example embodiment of a upward flow constructed wetland according to the teachings of the present invention.

To further improve biodegradation of chlorinated aliphatics, in addition to methane-oxidizing microorganisms, ammonia-oxidizing microorganisms can be added to an upward flow constructed wetland cells according to the teachings of the present invention.

The biogeochemical and hydro geological conditions within a wetland can change drastically over small vertical intervals. Therefore, a sampling approach offering a greater vertical resolution was desired as compared to an original nested piezometer system. A more rigid design for a porewater sampler than commonly used "peepers" were necessary due to the compact nature of the soil interval. The new pore-water sample chamber incorporated the advantage of dialysis bags placed inside a well at discrete depths. The new pore-water sample chamber includes small cylindrical units, each a few inches in length, housing a sample chamber and open on one side by a porous stainless steel plate. The units may be assembled in series (end-to-end) to a desired length, and can be easily lowered or pushed within the PVC casing of a well, and positioned at a screened interval of the well.

Solid PVC rod of 1.75-inch diameter was used to provide required structural support. The solid PVC rod was machined to a length of 4⅜-inches, and a cylindrical 1.25-inch diameter (internal volume: 19.5 mL) cavity was bored into the PVC rod from one side to create the sample cavity. The cylindrical cavity was rounded at the bottom in order to maximize the volume of the cavity. A 1.5-inch square porous stainless steel plate fastened with four #4-40 screws using standard helical inserts covers the sample cavity. A 1/16 inch thick VITON O-ring (1.25 inch inside diameter×1.375 inch outside diameter) was used under the porous stainless steel plate to provide a watertight seal. Sampling ports into the cavity of each chamber were provided on both ends of the pore-water sampler with septa material covering the ports being held in place with ¼ inch-20 vented screws and washers. The vented screws allowed access to the sample collection cavity with a sampling syringe and needle.

The samplers are designed to be chained together for insertion into a 2 inch monitoring well, enabling a pore-water sample to be obtained approximately every 3⅝ inches. A 2-inch outer diameter, ⅛ inch thick VITON washer placed between each sampler provides a tight fit against the well casing and therefore prevents vertical migration of the wetland water within the monitoring well. The VITON washer isolates each pore-water sampler and ensures that only the water within each targeted interval has contact with the respective pore-water sampler.

The teachings of the disclosed improvements for an upward flow constructed wetland will find application in other areas where beneficial biological processes are mimicked in a constructed system.

Various modifications to the invention as described may be made, as might occur to one with skill in the art of the invention, within the scope of the claims. Therefore, all contemplated example embodiments have not been shown in complete detail. Other embodiments may be developed without departing from the spirit of the invention or from the scope of the claims.

We claim:

1. An upward flow constructed wetland cell, comprising:
   (a) a membrane forming a bottom of the cell and isolating the cell from the environment;
   (b) a first zone above the membrane for entry of a supply of contaminated ground water;
   (c) a second zone above the first zone, comprising organic soil for anaerobic dechlorination of PCE to at least one of TCE, DEC and vinyl chloride;
   (d) a third zone above the second zone, comprising iron rich soil for iron reduction degradation of at least one of TCE, DEC and vinyl chloride; and,
   (e) a fourth zone above the third zone, comprising an oxygenated root zone, including:
      (i) methane-oxidizing microorganisms for aerobically destroying methane produced in lower zones, enabling co-metabolic destruction of at least one of TEC, DCE and vinyl chloride; and,
      (ii) ammonia-oxidizing microorganisms for aerobically destroying ammonia, enabling co-metabolic destruction of at least one of TEC, DCE and vinyl chloride;
   (f) at least one monitoring well extending vertically through at least one zone; and,
   (g) a pore-water sample chamber inserted inside the at least one monitoring well, the pore-water sample chamber comprising:
      (i) a solid rod having a long axis and a short axis;
      (ii) a cylindrical bore into the rod along the short axis forming a cavity;
      (iii) a porous plate covering the cavity; and,
      (iv) sampling ports along the long axis into the cavity.

\* \* \* \* \*